United States Patent
Belisle (10) Patent No.: US 9,488,616 B2
(45) Date of Patent: Nov. 8, 2016

(54) GELC-MS USING STAIN FREE TECHNOLOGY

(71) Applicant: Bio-Rad Laboratories, Inc., Hercules, CA (US)

(72) Inventor: Christopher Belisle, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/896,572

(22) Filed: May 17, 2013

(65) Prior Publication Data

US 2013/0306854 A1 Nov. 21, 2013

Related U.S. Application Data

(60) Provisional application No. 61/648,875, filed on May 18, 2012.

(51) Int. Cl.
| | | |
|---|---|---|
| *G01N 27/447* | (2006.01) |
| *H01J 49/00* | (2006.01) |
| *G01N 30/06* | (2006.01) |
| *G01N 33/68* | (2006.01) |
| *H01J 49/26* | (2006.01) |

(52) U.S. Cl.
CPC ........ *G01N 27/44721* (2013.01); *G01N 30/06* (2013.01); *G01N 33/6848* (2013.01); *H01J 49/0036* (2013.01); *H01J 49/26* (2013.01)

(58) Field of Classification Search
CPC .................................................. G01N 33/53
USPC ............................................. 435/4; 436/501
See application file for complete search history.

(56) References Cited

U.S. PATENT DOCUMENTS

| | | |
|---|---|---|
| 7,056,426 B2 | 6/2006 | Panattoni |
| 7,569,130 B2 | 8/2009 | Edwards et al. |
| 8,007,646 B2 | 8/2011 | Edwards et al. |
| 2004/0137526 A1 | 7/2004 | Hanash et al. |
| 2009/0170123 A1 | 7/2009 | Donate et al. |
| 2010/0089753 A1* | 4/2010 | Edwards et al. .............. 204/461 |

OTHER PUBLICATIONS

Gundry RL et al. Preparation of Proteins and Peptides for Mass Spectrometry Analysis in a Bottom-Up Proteomics Workflow. 2009. Current Protocols in Molecular Biology. p. 1-29.*
ThermoScientific. Tech Tip #51. 2009. p. 1-2.*
International Search Report and Written Opinion from PCT/US2013/041530, dated Oct. 7, 2013.
Bandhakavi S, et al. "Evaluation of Stain-Free Gels for GeLC-MS Applications." Poster presented at American Society of Mass Spectrometry Annual Meeting, May 20-24, 2012, Vancouver BC, Canada.
Edwards RA et al. "The light-induced reactions of tryptophan with halocompounds." *Photochem. & Photobiol.* 75, 362-368, 2002.
Fang Y et al. "Quantitative analysis of proteome coverage and recovery rates for upstream fractionation methods in proteomics." *J. Proteome Res.* 9, 1902-1912, 2010.
Ladner CL et al. "Identification of trichloroethanol visualized proteins from two-dimensional polyacrylamide gels by mass spectroscopy." *Anal. Chem.* 78, 2388-2396, 2006.
Ladner CL et al. "Development of indole chemistry to label tryptophan residues in protein for determination of tryptophan surface accessibility." *Protein Sci.* 16, 1204-1213, 2007.
Liu N, et al. "Compatibility of Criterion Stain Free™ Gel Imaging System with Mass Spectrometric Protein Analysis." Bio-Rad Bulletin 5810. Copyright 2008.
McDonald K et al. "In-Gel Protein Quantitation Using the Criterion Stain-Free™ Gel Imaging System." Bio-Rad Bulletin 5782. Copyright 2008.
Piersma SR et al. "Workflow comparison for label-free, quantitative secretome proteomics for cancer biomarker discovery: method evaluation, differential analysis, and verification in serum." *J. Proteome Res.* 9, 1913-1922, 2010.
Rappsilber J et al. "Stop and go extraction tips for matrix-assisted laser desorption/ionization, nanoelectrospray, and LC/MS sample pretreatment in proteomics." *Analytical Chemistry* 75, 663-670, 2003.
Sechi S and Chait BT. "Modification of cysteine residues by alkylation. A tool in peptide mapping and protein identification." *Analytical Chemistry* 70, 5150-5158, 1998.
Shevchenko A et al. "Mass spectrometric sequencing of proteins silver-stained polyacrylamide gels." *Analytical Chemistry* 68, 850-858, 1996.

* cited by examiner

*Primary Examiner* — Paul Holland
(74) *Attorney, Agent, or Firm* — Kilpatrick Townsend and Stockton LLP (57) ABSTRACT

Disclosed herein is a method of preparing a protein sample for mass spectroscopy. The method includes separating proteins of the sample on an electrophoresis gel; contacting the proteins with a halo-substituted organic compound; exposing the gel to UV light; detecting fluorescence emitted from the electrophoresis gel; excising at least one portion of the electrophoresis gel based upon the detected fluorescence, wherein said at least one portion contains proteins of the protein sample; and subjecting proteins from the at least one portion to mass spectroscopy. Using this method, more proteins can be identified by GeLC-MS than when the electrophoresis gel is treated with a protein stain or subjected to the gel handling steps accompanying such treatment.

20 Claims, 3 Drawing Sheets

GELC-MS USING STAIN FREE TECHNOLOGY

CROSS-REFERENCES TO RELATED APPLICATIONS

The present application claims priority from U.S. Provisional Application No. 61/648,875, entitled "GeLC-MS Using Stain-Free Technology" and filed May 18, 2012, the entire contents of which are herein incorporated by reference for all purposes.

BACKGROUND OF THE INVENTION

The growing field of proteomics is concerned with identifying large numbers of proteins in living organisms, understanding the functions and interactions of these proteins, and characterizing how the repertoire of proteins in an organism is modulated by factors such as developmental stage, disease state, and environment. Proteomics also aims to address how the set of proteins needed to sustain life varies among individual cells, cell types, tissues, individual organisms, groups of organisms, species, and groups of species. An important tool in experimental proteomics is mass spectroscopy, which allows identification of many proteins from complex biological samples. In many mass spectroscopy protocols, proteins or protein fragments from a sample are ionized and detected on the basis of mass. The detected masses are then compared, through a database search, with the predicted masses of proteins (or portions thereof) thought to exist in the organism from which the sample is obtained. Matches between detected and predicted masses allow the amino acid sequences of the particular proteins present in the sample to be inferred.

Crude biological samples that contain diverse populations of proteins are often not pure enough to submit directly to mass spectroscopy. These samples can also contain carbohydrates, lipids, nucleic acids, and other contaminants, which, if not removed prior to data acquisition, can lead to artefactual peaks on a mass spectrum and masking of the peaks arising from proteins of interest. Furthermore, proteins cannot be easily identified by mass spectroscopy if too many different proteins are passed through the mass spectrometer at once. This can lead to highly complex mass spectra where individual peaks, and in turn, individual protein sequences cannot be easily resolved. Accordingly, biological samples often must be processed for proteomic mass spectroscopy, such that proteins are separated from contaminants and from each other before being injected into the mass spectrometer.

Gel electrophoresis and liquid chromatography (LC) are two techniques that are often used together for this purpose. Gel electrophoresis separates proteins on the basis of mass, size, or isoelectric point, while liquid chromatography can separate molecules on the basis of hydrophobicity, hydrophilicity, size, charge, affinity for a binding partner, and other characteristics (depending on the nature of the chromatography column). Using the two techniques in series allows proteins to separated from each other and from any contaminants on the basis of two or more orthogonal characteristics, so that they can be more easily analyzed and identified by mass spectroscopy. In practice, a protein sample is run on an electrophoresis gel, and the resulting separation allows extraction of specific portions of the sample from corresponding regions of the gel. The portions are then passed through a liquid chromatography column one by one and fed into a mass spectrometer, and multiple spectra can be acquired as the elution of proteins from the column progresses. The use of gel electrophoresis in conjunction with liquid chromatography and mass spectroscopy is referred to herein, and in the art, as GeLC-MS.

To extract proteins from a gel, the proteins must first be detected after electrophoresis. Detection tells the practitioner where proteins are located in the gel and allows him or her to identify specific portions of the protein sample. In the case of a two-dimensional (2D) gel, i.e. an electrophoresis gel used to separate proteins in two orthogonal directions on the basis of two different physical properties, detection reveals the locations of individual proteins or groups of proteins, which appear as spots. In the case of a one-dimensional (1D) gel, where separation occurs in only one direction, detection reveals the farthest extent that proteins have migrated from the wells in which they were loaded, the distribution of proteins along the direction of migration, and the boundaries of lanes. Here, proteins appear as bands or as a streak on the gel. Specific portions of the protein sample can then be chosen as desired by the practitioner for extraction, and the information provided by detection can be used subsequently, for example to interpret mass spectroscopy data.

Detection of proteins in electrophoresis gels is frequently performed using colored or fluorescent protein stains such as Coomassie Brilliant Blue or SYPRO Ruby. These stains can bind to proteins non-covalently, in a manner that is largely independent of amino acid sequence, and can be visualized upon illumination with specific wavelengths of light. Protein stains allow robust and sensitive detection, but hinder the rapid processing of biological samples for proteomic mass spectroscopy. The process of applying the stain to the gel (staining) prior to detection can take hours. Similarly time consuming is the removal of the stain after detection (destaining), which can be necessary in order to obtain accurate masses of proteins and protein fragments. Staining and destaining involve agitation of the gel, prolonged immersion of the gel in an aqueous buffer, and frequent changes of this buffer. During these processes, some proteins (particularly low-molecular-weight and hydrophilic proteins) can diffuse out of the gel and into the buffer, thereby becoming lost to subsequent analysis. Use of protein stains, and the accompanying gel handling, can therefore reduce the number of proteins that can be identified in GeLC-MS.

BRIEF SUMMARY OF THE INVENTION

Provided herein are methods of preparing a protein sample for mass spectroscopy and identifying one or more protein in a sample.

In some embodiments, a method of preparing a protein sample for mass spectroscopy is provided. The method includes providing an electrophoresis gel including the protein sample, wherein proteins of the protein sample have been separated by electrophoresis; contacting the protein sample with a halo-substituted compound; exposing the electrophoresis gel to UV light; detecting fluorescence emitted from the electrophoresis gel; excising at least one portion of the electrophoresis gel based upon the detected fluorescence, wherein said at least one portion contains proteins of the protein sample; and subjecting proteins from the at least one portion to mass spectroscopy.

In one embodiment of the method, the halo-substituted compound is a component of the electrophoresis gel and the contacting occurs upon separating proteins of the protein sample by electrophoresis.

In another embodiment, the halo-substituted compound is chloroform, trichloroethanol, trichloroacetate, or 3-bromo-1-propanol.

In yet another embodiment, the UV light has a wavelength in the range of about 200 nm to about 400 nm.

In still another embodiment, the fluorescence emitted from the electrophoresis gel arises from covalently modified tryptophan residues in proteins of the protein sample.

In yet another embodiment, the exposing and detecting occur simultaneously.

In still another embodiment, the electrophoresis gel is a one-dimensional (1D) gel.

In some embodiments of the method, the number of portions of the electrophoresis gel excised is in the range of about 1 to 30, 2 to 20, 5 to 15, or 6 to 12.

In one embodiment of the method, the at least one portion of the electrophoresis gel is excised from one lane of the electrophoresis gel. In another embodiment, multiple portions are excised from the electrophoresis gel and the portions are together substantially coextensive with one lane of the electrophoresis gel. In yet another embodiment, the at least one portion of the electrophoresis gel contains proteins with covalently modified tryptophan residues.

In some embodiments of the method, the proteins subjected to mass spectroscopy include proteins that would be absent if the electrophoresis gel were treated with a protein stain.

In other embodiments, the method further includes detecting proteins by mass spectroscopy that would be absent if the electrophoresis gel were treated with a protein stain. In these embodiments, the protein stain can be selected from the group consisting of COOMASSIE™ Brilliant Blue, Ponceau S, and SYPRO RUBY™.

In some embodiments, the method further includes contacting the at least one portion of the electrophoresis gel with a protease or alkylating agent. In one such embodiment, the protease is trypsin. In another such embodiment, the alkylating agent includes iodoacetamide.

In one embodiment, the method further includes subjecting proteins, or fragments thereof, from the at least one portion of the electrophoresis gel to further separation by liquid chromatography.

In another embodiment, the mass spectroscopy is LC-MS.

In yet another embodiment, the method further includes detecting the masses of proteins or fragments thereof from the at least one portion of the electrophoresis gel by mass spectroscopy; and, using a computer, determining the amino acid sequences of said proteins or fragments thereof, wherein said determining takes into account any changes in the masses of tryptophan residues due to covalent modifications.

Further provided herein is a method of identifying one or more protein in a sample. The method includes performing GeLC-MS using a stain-free gel, wherein one or more amino acid in the protein is modified by the stain-free gel. In some embodiments, the method includes: electrophoretically separating the sample into a lane of the stain-free gel; isolating the lane, or portion thereof, from the gel; digesting the protein in the lane or portion thereof; and performing mass spectrometry (MS) on the digested protein. In one such embodiment, the performing comprises correlating MS data of the digested protein to a database of protein mass and charges.

DETAILED DESCRIPTION OF THE INVENTION

Introduction

The inventors have surprisingly discovered that more proteins in a protein sample can be identified by GeLC-MS when the electrophoresis gel is not treated with a protein stain or subjected to the gel handling steps accompanying such treatment. Proteins are detected on the gel instead using a halo-substituted organic compound, which reacts with tryptophan residues of the proteins upon exposure to UV light. Tryptophan residues so reacted are fluorescent and can be used to locate portions of the protein sample on the gel. These portions of the protein sample can then be extracted from the gel, such as by excising portions of the gel, further processed (e.g. fragmented with trypsin), and subjected to liquid chromatography and mass spectroscopy. When using this stain-free method of detecting proteins on the gel, the inventors identified particular proteins by GeLC-MS that could not be identified when detecting proteins with a stain, and identified more proteins in total.

Methods

Provided herein are methods of preparing a protein sample for mass spectroscopy. The methods include separating proteins of the protein sample on an electrophoresis gel, detecting the proteins using halo-substituted organic compounds and UV light, and excising portions of the gel for further processing and submission to mass spectroscopy (e.g. GeLC-MS). Such further processing can include fragmentation of proteins in the excised portions of the gel, reduction and alkylation of these proteins, removal of the proteins from the gel material, and purification of the proteins by liquid chromatography. Also provided are methods of identifying such proteins by mass spectroscopy while accounting for changes in the mass of tryptophan residues due to reaction with halo-substituted organic compounds.

The protein sample to be analyzed by mass spectroscopy can be obtained from any source. Examples of potential sources include cells, groups of cells, tissues, or entire organisms, living or dead. The sample can be a cell lysate, tissue homogeneate, or sample of blood, saliva, urine, or other bodily fluid, among other possibilities. It will be appreciated that protein samples from different sources vary in the number, identities, and abundances of proteins that they contain, and that many of these parameters will not be known at the time the sample is acquired. Indeed, elucidating these parameters is often the goal of the proteomic inquiry for which GeLC-MS is used as a tool. By including several processes for separating proteins from each other and from contaminants, as discussed above, GeLC-MS is suitable for analyzing complex protein samples and comparing these samples with each other. Comparisons can be made between samples from different biological sources, such as different adult humans, humans of different ages, diseased and healthy humans, humans of different races or ethnicities or from different parts of the world, humans undergoing different treatments for diseases, humans undergoing treatments vs. humans not undergoing treatments, humans vs. non-human mammals, or any variable vs. a control. Other examples will be readily apparent to those of skill in the art.

The number of different proteins that will most often be present in a "complex sample" as the term is used herein will be about 50 or more, often within from about 50 to about 100,000, and in many cases from about 100 to about 50,000. The molecular weights of these proteins can vary widely, and many such samples will have molecular weights ranging from those having less than twenty amino acid residues to those having 1,000 or more, including as many as 5,000. Likewise, the number of tryptophan residues among the proteins in a single sample can range from as little as zero to as high as 5%.

Once obtained, a protein sample may require preparation before it can be run on an electrophoresis gel and further processed for mass spectroscopy. Such preparation can include e.g. centrifuging or filtering the sample to remove tissue fragments, membranous structures, or other large contaminants; concentrating the sample into a smaller volume by application of a pressure differential; or adding chemicals to the sample such as protease inhibitors or buffering agents. In particular, in some embodiments the sample is added to or resuspended in a buffer similar to that in which the electrophoresis gel is run, in terms of pH or salt concentrations. This ensures that proteins of the sample will enter the electrophoresis gel and migrate within it in an efficient, reproducible manner. Other preparatory steps will be apparent to those skilled in the art. It will be appreciated that some preparatory steps can reduce the number of proteins loaded onto the electrophoresis gel and ultimately identified by mass spectroscopy.

Any electrophoresis gel can be used in the methods described herein. For example, the gel can be of any dimensions, have any number of lanes, and be prepared (poured) by hand or by machine. In some embodiments, the gel comprises polyacrylamide, which can be present at any percentage or concentration, including at more than one concentration (e.g. in stacking and resolving portions of the gel) or at a gradient of concentrations. The gel can also comprise a denaturing agent such as sodium dodecyl sulfate, as well as buffering agents such as tris(hydroxymethyl) aminomethane (Tris), glycine, or tricine. Other common constituents of electrophoresis gels, particularly gels used to separate complex protein samples, will be apparent to the skilled artisan.

In some embodiments, the gel includes additives that allow proteins to migrate through the gel faster and at higher applied voltages than would be practicable in the absence of these additives. The additives also improve separation of proteins for mass spectroscopy by preventing the duplication of bands, which can result from gaps or undesired interactions between the gel and the plates between which it is held (see e.g. U.S. Pat. No. 7,056,426). Examples of such additives include poly(vinyl alcohol), agarose, poly(vinyl pyrrolidone), poly(ethylene glycol), poly(ethylene oxide), poly(propylene glycol), poly(propylene glycol)/poly(ethylene glycol) copolymers, and linear polyacrylamide. Electrophoresis gels containing one or more of these additives are available from Bio-Rad under the name 'TGX'.

In some embodiments, the gel also includes a halo-substituted organic compound as a constituent. As is discussed below, this compound can react in situ with tryptophan residues in proteins of the sample, resulting in a detectable fluorescent product. The reaction, and the associated reagents, apparatus, and methods used to perform the reaction and detect products thereof, are sometimes referred to by the name 'Stain-Free™' (Bio-Rad).

The electrophoresis gel can be run using any techniques desired, and using any available materials or apparatus. In standard practice, the gel is contacted with an electrolyte-containing buffer and placed between two electrodes, and a current is applied between the electrodes. Running, or electrophoresis, causes proteins of the protein sample to migrate within the gel and become separated from each other according to molecular weight, size, or charge. Electrophoresis can also separate proteins from contaminants that may have been loaded onto the gel along with the protein sample. Such contaminants can fail to enter the gel when the current is applied, can diffuse from the gel into the surrounding buffer, or can pass through the gel more slowly or quickly than proteins of interest in the sample. For convenience and if desired, a molecular weight marker can be loaded into the gel along with the protein sample, allowing the practitioner to track the positions of proteins in the sample during or after migration.

Both 1D and 2D electrophoresis gels can be used in embodiments of the invention. (Note that the terms 'one-dimensional', '1D', 'two-dimensional', and '2D', as applied herein to electrophoresis gels, do not denote the number of dimensions of the gels themselves but rather the number of dimensions of protein migration within the gels.) 1D gels allow more straightforward extraction of proteins after electrophoresis and can be chosen when the practitioner wants to submit the entire protein sample, or large portions thereof, to mass spectroscopy. 2D gels provide more extensive separation of proteins and can be chosen when the practitioner wants to analyze a smaller portion of the protein sample or a specific set of proteins. Proteins of the sample become distributed over a wider area after running on a 2D gel, and so greater sensitivity of detection is needed in this case in order to extract all proteins of interest.

After the gel has been run, proteins can be made detectable by contacting the proteins with a halo-substituted organic compound and exposing the gel to UV light. As disclosed by Edwards et al. in U.S. Pat. No. 7,569,103 B2 (Aug. 4, 2009) and U.S. Pat. No. 8,007,646 B2 (Aug. 30, 2011), and elsewhere, this procedure causes a UV-induced reaction between the indole moiety of tryptophan and the halo-substituted organic compound. Reacted tryptophan residues are covalently modified and fluorescent, undergoing excitation at the same wavelengths used to induce the reaction and emitting in the visible range. In some embodiments, the halo-substituted compound is added to the gel when it is poured, so that proteins come into contact with the compound when the gel is run. In these embodiments, the gel can simply be exposed to UV light, thereby allowing the compound to react with tryptophan residues of the proteins in the gel, and fluorescence can be detected. Exposure and detection can occur simultaneously. In other embodiments, discussed below, the halo-substituted organic compound is absent from the gel when it is initially poured, but can be added by immersing the gel in a solution of the compound and allowing the compound to diffuse into the gel. A skilled artisan will recognize that no matter how the halo-substituted organic compound is brought into contact with proteins in the gel, the gel may need to be removed from the apparatus in which it is run for UV exposure, fluorescence detection, and subsequent manipulation.

A variety of halo-substituted organic compounds can be used in stain-free gel technology as described herein.

Indeed, any halo-substituted organic compound can be used that will enter into a chemical reaction with tryptophan to form a product that fluoresces upon exposure to excitation light. Halo-substituted organic compounds of particular interest are trihalo compounds, most notably trichloro compounds and those with molecular weights of 200 or less. Trihaloaliphatic alcohols, trihaloaliphatic acids, trihaloaliphatic amines, and trihaloalkanes are all useful. Specific examples are chloroform, trichloroacetic acid, and trichloroethanol. Halo-substituted organic compounds can be used individually or in combinations, such as for example combinations of two or three such compounds in approximately equal molar proportions.

The halo-substituted compounds used in the practice of the present invention are preferably used in the absence of any protein stains so that the procedure is truly stain-free. By "protein stains" is meant compounds that are color-bearing or fluorescent on their own, i.e., in the absence of any reaction with amino acid residues, and that adhere to proteins by means other than a coupling reaction. Many such stains exist, examples of which are COOMASSIE™ Brilliant Blue (BASF Aktiengesellschaft, Ludwigshafen, Germany), Ponceau S (Sigma-Aldrich, St. Louis, Mo., USA), and SYPRO RUBY™ (Sigma-Aldrich).

Application of the halo-substituted compound to the proteins can be achieved by conventional means. When the proteins are in a gel, for example, the gel can be immersed in a solution of the halo-substituted compound. The choice of solvent and the concentration of the halo-substituted compound in the solution can vary widely and can readily be optimized in terms of the intensity of the signal that is ultimately produced. Any solvent or combination of solvents that will dissolve the compound can be used. Water or mixtures of water and a lower-molecular weight alcohol such as methanol, ethanol, or isopropanol, will suffice in most cases. Concentrations may range from about 1% by weight to about 30% by weight, or in many cases from about 5% to about 20% by weight. In terms of the amount of the halo-substituted compound itself in the gel, this can vary widely as well, although effective and efficient results can generally be obtained with about 0.2% to about 2.0% of the halo-substituted compound in the gel, and in many cases from about 0.1% to about 0.5%, by volume.

The reaction times and conditions for the reaction between the proteins (i.e., their tryptophan residues) and the halo-substituted compounds can vary widely. Contact can be made at room temperature (70-75° F.), although higher and lower temperatures can also be used, provided that no additional or unwanted reactions occur at such temperatures, no phase changes occur, and the reaction occurs at an economically viable reaction rate. The contact time can likewise vary. At room temperature, effective results can generally be achieved with a contact time within the range of about thirty seconds to about thirty minutes, and in many cases optimal efficiency is achievable with a contact time of from about 1 minute to about ten minutes. When contact is achieved by immersion of a gel in a solution of the halo-substituted compound, the gel can be rinsed with water to remove excess solution following the contact time.

Once contact is made and excess halo-substituted compound removed, the reaction between the protein and the compound can be completed by irradiating the medium in which they reside with UV (ultraviolet) light of a sufficient intensity and duration to both cause the reaction to occur and to produce a fluorescent emission that can be detected and quantified. The ease of detection and quantification may vary with the type of detector used. Useful wavelengths will generally include those that reside within the range of from about 200 nm to about 400 nm, and an exposure time of from about thirty seconds to about thirty minutes, or more efficiently from about 1 minute to about ten minutes, will generally provide adequate results. Irradiation can be achieved by either transillumination or epi-illumination, and detection can be achieved by imaging such as by the use of photography, or by electronic sensors such as photodiodes, charge-coupled device (CCD) detectors, or complementary metal-oxide semiconductor (CMOS) detectors. Digital results can be analyzed by conventional imaging software. Irradiation with excitation light for purposes of detection of emissions can also be performed after the coupling reaction has occurred, either for an initial detection or for repeat detections.

The detected tryptophan fluorescence can then be used to guide the extraction of proteins of interest from the gel. In some embodiments, extraction involves first excising portions of the gel containing proteins of interest. Excising portions of the gel can be performed as desired, for example by making cuts in the gel around each portion, thereby completely separating the portion from the rest of the gel (as well as any other portions) and allowing the portion to be removed. The cuts can be made using a razor blade or similar laboratory implement, and can be made at the edges of regions of the gel that emit fluorescence. The cuts can thus be used to define and excise portions of the gel that are fluorescent and presumably contain protein, so that only portions with these characteristics are excised, and parts of the gel lacking protein are left behind. The cuts can be made while simultaneously illuminating the gel and observing fluorescence, by referring to an image (e.g. photograph) of fluorescence emitted from the gel, by referring to fiducial marks in the gel or in the surface underlying it, or using other methods. Indeed, any method can be used to excise one or more portions of the electrophoresis gel based upon the detected fluorescence, provided that the method does not rely on a protein stain such as those recited above.

The number of portions excised, the locations of these portions within the gel prior to excision, and the parts of the protein sample that these portions contain, can be all chosen as desired. In some embodiments, only one portion of the gel corresponding to a subset of proteins in the sample is excised. This portion can correspond to a set of fluorescent bands in one lane of a 1D gel, and can be identified from the banding pattern in the lane or by making reference to an adjacent protein standard reporting molecular weight. Indeed, portions of the gel can be excised according to molecular weight, and information about the molecular weights of proteins contained in the portion (e.g., the range of weights) can be used subsequently in analysis of mass spectroscopy data. A single portion of a 2D gel can correspond to a set of fluorescent spots or an area defined with respect to such spots. For both 1D and 2D gels, excised portions can be cut to any shape or size.

In other embodiments, multiple portions of the gel are excised. An entire lane of a 1D gel can be excised by first cutting along the edges of the lane, as detected by tryptophan fluorescence, and then cutting the resulting strip into smaller portions. Here, the portions together are substantially coextensive with the lane and contain substantially all proteins in that lane. If the entire protein sample was loaded in the lane, and the gel was not run long enough to allow proteins to migrate through the entire length of the gel and exit, then the portions together also contain substantially all proteins of the sample. Multiple portions can be similarly excised from a 2D gel by making a square or rectangular grid of cuts in the gel and removing pieces of the gel resulting from the cuts, for example.

In some embodiments, multiple portions are excised from one lane of a 1D gel, such as by cutting up a strip that contains the lane as described above. Preferably, the portions correspond to different regions (e.g. molecular weight ranges) along the direction of migration of proteins in the gel, so that the portions are distinguished from each other by how far the proteins within them have migrated. Accordingly, the portions reflect the separation of proteins achieved by electrophoresis. Once the lane of the gel is identified, portions can be cut from the lane as desired, for example to have equal sizes (e.g. 0.5, 1, 2, or 5 cm along the direction of migration). Alternatively, the portions can be cut so that the difference in molecular weight between the highest and lowest molecular weight proteins in each portion is roughly constant. For example, each portion spans 50, 100, 200, or 500 kDa in molecular weight. In this case, making reference to a molecular weight standard can be helpful, and portions containing higher molecular weight proteins are cut smaller than those containing lower molecular weight proteins. Finally, the portions can be cut according to the pattern of bands in the lane, for example to keep certain bands together or to prevent one portion from having too much or too little protein (using tryptophan fluorescence as a proxy for protein density).

When excising multiple portions from one lane of an electrophoresis gel for GeLC-MS, the number of portions excised determines how much protein is contained in each portion and, in turn, how much protein is submitted to mass spectroscopy per portion. All else being equal, excising more portions results in smaller portions, less protein per portion and clearer, less complex mass spectra for the proteins in each portion. However, because proteins are submitted to mass spectroscopy portion by portion, i.e. one portion at a time, excising more portions also requires more time for data acquisition. In some embodiments, the number of portions of the electrophoresis gel excised in the range of about 1 to 30, 2 to 20, 5 to 15, or 6 to 12.

Once portions of the gel have been excised, the portions can be further processed before subjecting proteins in each portion to liquid chromatography and mass spectroscopy. In some embodiments, the portions can be treated with a protease to cleave proteins into fragments, which can be more readily identified by mass spectroscopy than whole proteins. One protease for this purpose is trypsin, which catalyzes the hydrolysis of peptide bonds adjacent to lysine or arginine residues and can be applied in-gel (see e.g. Shevchenko et al., *Analytical Chemistry* 68: 850-858, 1996). Examples of other proteases that can be used with mass spectroscopy are chymotrypsin, Lys-C, and Glu-C, and elastase. In some embodiments, the portions are treated with one or more reagents that target cysteine residues. Such reagents include dithiothreitol or beta-mercaptoethanol, which reduce disulfide bonds, and iodoacetamide, which alkylates cysteine side chains (see e.g. Sechi and Chait, *Analytical Chemistry* 70: 5150-5158, 1998). Use of these reagents can make the identification of cysteine-containing proteins and protein fragments by mass spectroscopy more straightforward.

Proteins can be extracted from the electrophoresis gel or portions thereof as desired. In some embodiments, for example, holes can be punched in a gel portion using a hollow implement such as pipette tip or syringe needle, and liquid can be passed through the implement and into a liquid chromatography column, thereby loading the column with proteins from the gel portion. The implement can packed with solid materials, such as reversed-phase beads, that block gel material captured in the implement from passing into the column, and that facilitate the diffusion of proteins from the gel material into the liquid stream (see e.g. Rappsilber et al., *Analytical Chemistry* 75: 663-670, 2003).

In other embodiments, proteins are extracted from portions of the gel separately from, and prior to, loading the liquid chromatography column. For example, polyacrylamide gels can be dissolved by treatment with perchloric acid and hydrogen peroxide, and proteins in the gel can then be isolated in a liquid fraction. Alternatively, proteins can be drawn out of the gel by electroelution. These and other methods of extracting proteins from gels are reviewed, for example, in Sambrook and Russell, *Molecular Cloning: A Laboratory Manual* ($3^{rd}$ ed.), New York: Cold Spring Harbor Laboratory Press, 2001. A skilled artisan will recognize that proteins can be treated with proteases, reducing agents, or alkylating agents (as described above) before or after extraction from a gel, and considerable flexibility exists in methods to prepare protein samples for liquid chromatography from gel portions.

Any apparatus for liquid chromatography can be used in the methods described herein. In some embodiments, the electrophoresis gel and liquid chromatography apparatus provide complementary or orthogonal types of separation between proteins of the sample. That is, proteins are first separated on the electrophoresis gel, and then become further separated upon loading proteins from portions of the gel into the liquid chromatography column. An example of a suitable liquid chromatography column is a C18 reverse-phase column, where protein retention is governed by hydrophobicity. Other examples include size exclusion, gel filtration, normal-phase, ion exchange, affinity, and mixed-mode columns. Using liquid chromatography to perform protein purification or separation is reviewed in *Introduction to Modern Liquid Chromatography*, $3^{rd}$ ed., New York: Wiley, 2010 and elsewhere.

Proteins eluting from the liquid chromatography column can be submitted directly to mass spectroscopy, as is the common practice in GeLC-MS. In some embodiments, the column is mounted in-line with a nanospray source and the mass spectrometer. In other embodiments, the column eluate is subjected to electrospray ionization. Methods and apparatus for coupling a liquid chromatography column to a mass spectrometer are well known and are reviewed in, for example, *Protein and Peptide Analysis by LC-MS*, Cambridge, UK: Royal Society of Chemistry, 2011. Using liquid chromatography as the sample source to feed a mass spectrometer, and performing mass spectroscopy with the spectrometer in this configuration, is termed 'LC-MS' herein and in the art. In some embodiments, the mass spectroscopy for which the protein sample is prepared is LC-MS. Matrix-assisted laser desorption/ionization, thermal ionization, chemical ionization, inductively coupled plasma ionization, quadrupole ion trapping, orbital ion trapping, time-of-flight analysis, Fourier transform ion cyclotron resonance analysis, tandem mass spectroscopy, and any other technique or instrumental configuration in mass spectroscopy can be used in embodiments of the present invention.

Proteins of the protein sample can be identified from mass spectroscopy data using standard methods. A mass spectrum provides information about the masses and ionization states of individually detected molecular fragments. For each fragment, a set of candidate amino acid sequences can be identified that are consistent with the data for the fragment, and this set can narrowed by comparing candidate sequences with reference sequences from a database. The database can include wild-type amino acid sequences for the species from which the sample was obtained, sequences from a related species, or sequences generated by translating genomic DNA in different open reading frames, for example. A match between a candidate sequence and a reference sequence is declared when the number of candidate sequences can be reduced to one (i.e. the data for a fragment is consistent with only one sequence in the database), or when a candidate sequence can be chosen with a desired level of certainty. This level of certainty can be reached by comparing data between fragments—for example, if several fragments have masses consistent with sequence portions of the same protein, then they all likely originate from that protein.

Analysis of mass spectroscopy data is typically performed on a computer and takes into account additional factors that can further increase the certainty with which matches are declared. One of these factors is the fragmentation pattern of protein molecules, which can be predicted based on the cleavage pattern of any protease with which the protein sample is treated, or based on the ionization method used. Another factor is the range of molecular weights of proteins submitted to mass spectroscopy, which can be estimated as described above when excising a portion of the electrophoresis gel containing the proteins. A third factor is covalent modifications of these proteins. For example, alkylation of a cysteine residue with iodoacetamide, or reaction of a tryptophan residue with a halo-substituted organic compound, results in addition of a chemical moiety to the residue with a measurable mass. Accordingly, protein fragments that contain covalently modified residues have different (in many cases larger) masses than fragments lacking modified residues.

Upon reacting with a halo-substituted organic compound, a tryptophan-containing protein undergoes a change in mass that depends on the identity of the compound. For example, the mass increases by 28 Da per modified tryptophan when the compound is chloroform, 44 or 58 Da when the compound is trichloroethanol, 44 Da when the compound is trichloroacetate, and 58 Da when the compound is 3-bromo-1-propanol. These masses correspond to addition of a formyl (+28 Da), carboxylic acid (+44 Da), hydroxyethanone (+58 Da), or propanol (+58 Da) moiety to the indole ring of tryptophan (see e.g. Edwards et al., *Photochemistry & Photobiology* 75: 362-368, 2002, and Ladner et al., *Protein Science* 16: 1204-1213, 2007). In addition, the mass of the protein can increase by 32 Da upon the UV-induced addition of $O_2$ to tryptophan, a process that yields N-formylkynurenine and does not require the participation of a halo-substituted organic compound. In the methods described herein, in order to identify tryptophan-containing proteins in the protein sample, the change in mass due to covalent modification can be accounted for as desired. For example, the mass of an added moiety can be appropriately added to or subtracted from the measured mass of a protein fragment, and the result can be compared with the calculated masses of amino acid sequences from a database.

The reaction of tryptophan with a halo-substituted organic compound, like any chemical reaction, is not completely efficient and depends on the surface accessibility of tryptophan residues, among other factors. Accordingly, proteins containing multiple tryptophan residues can undergo varying extents of modification. For example, a protein containing two tryptophan residues can have zero, one, or two residues modified after reaction with a halo-substituted organic compound. The inventors have found evidence that all three products can be detected using mass spectroscopy.

In some embodiments, proteins are identified by detecting protein fragments that correspond to different numbers of tryptophan residues being modified. For example, in the case of the protein with two tryptophan residues, the protein will not be positively identified unless protein fragments are detected that are consistent with all three products being present in the sample. Similar rules can be proposed for proteins having any number of tryptophan residues.

Computer Systems

Many of the methods disclosed herein can be performed on a computer or using a computer system. These methods include, without limitation: identifying candidate amino acid sequences consistent with mass spectroscopy data; searching a database of reference amino acid sequences; comparing candidate and reference amino acid sequences, or masses thereof; adding or subtracting a constant (e.g. the mass of a chemical moiety) to the mass of a protein fragment; and otherwise adjusting the mass of a protein fragment to account for covalent modifications. Computer algorithms for performing these methods can be encoded using established programming languages and structures, and executed on standard computer systems. Further disclosure of computer systems that may be used in embodiments of the invention is provided below.

Figure 1:
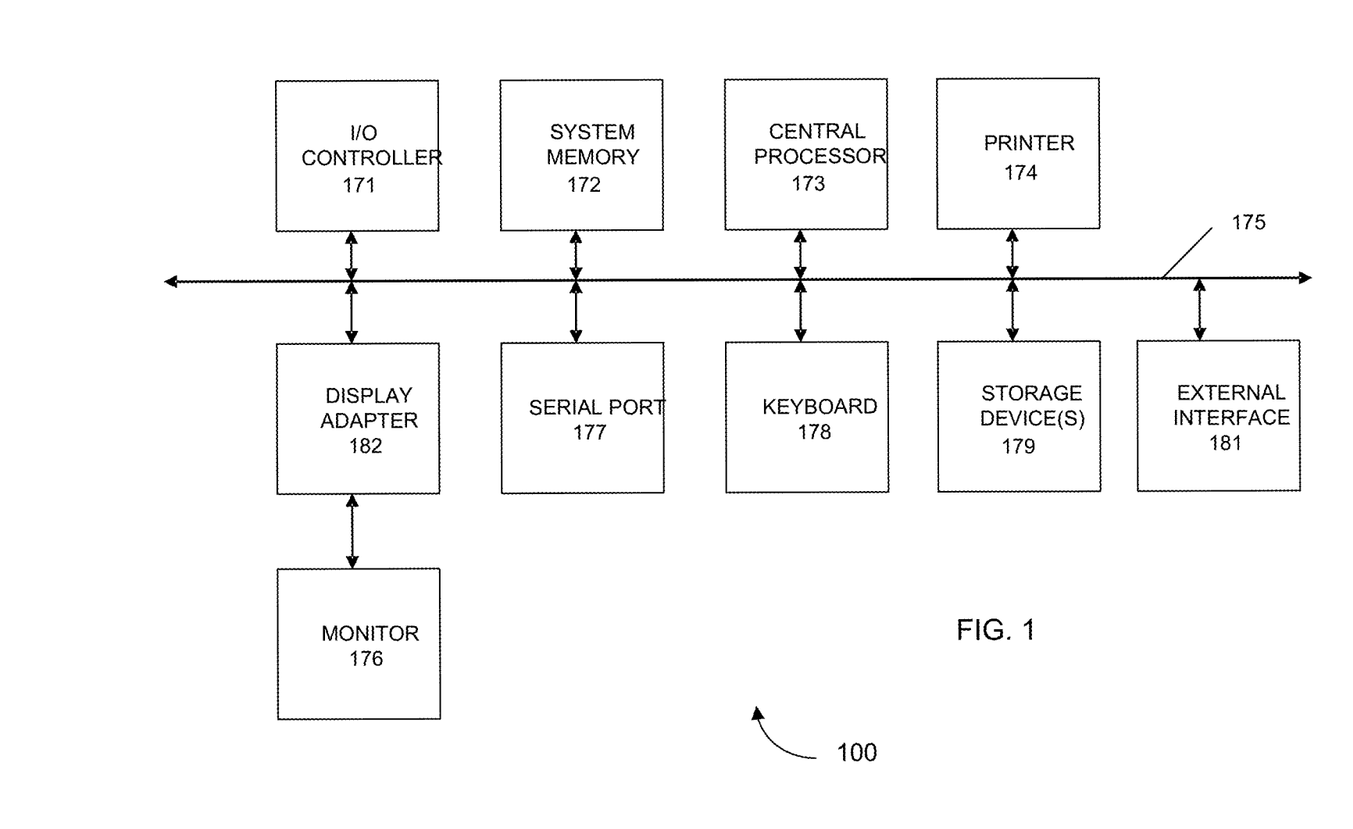
FIG. 1 shows a computer system for use with some embodiments of the invention.

Any of the computer systems mentioned herein may utilize any suitable number of subsystems. Examples of such subsystems are shown in FIG. 1 in computer apparatus 100. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 1 are interconnected via a system bus 175. Additional subsystems such as a printer 174, keyboard 178, storage device(s) 179, monitor 176, which is coupled to display adapter 182, and others are shown. Peripherals and input/output (I/O) devices, which couple to I/O controller 171, can be connected to the computer system by any number of means known in the art, such as serial port 177. For example, serial port 177 or external interface 181 (e.g. Ethernet, Wi-Fi, etc.) can be used to connect computer system 100 to a wide area network such as the Internet, a mouse input device, or a scanner. The interconnection via system bus 175 allows the central processor 173 to communicate with each subsystem and to control the execution of instructions from system memory 172 or the storage device(s) 179 (e.g., a fixed disk, such as a hard drive or optical disk), as well as the exchange of information between subsystems. The system memory 172 and/or the storage device(s) 179 may embody a computer readable medium. Any of the data mentioned herein can be output from one component to another component and can be output to the user.

A computer system can include a plurality of the same components or subsystems, e.g., connected together by external interface 181 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that some of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

The methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

EXAMPLE

Figure 2:
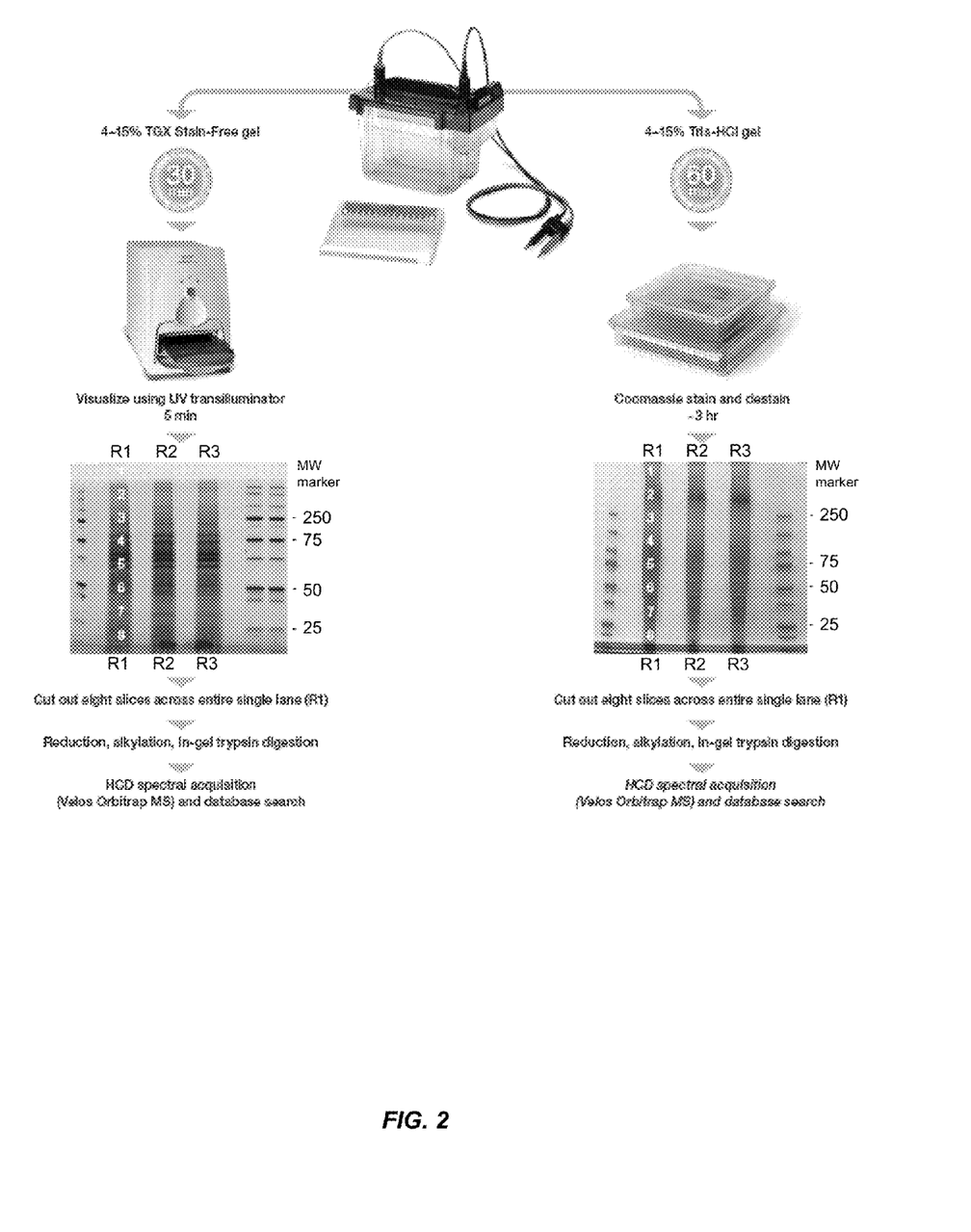
FIG. 2 shows a comparison of the 3T3 cell lysate separated on Criterion gels. 50 μg of mouse 3T3 lysate electrophoresed on Criterion 4-15% TGX Stain-Free gel (left) or 4-15% Tris-HCl gel (right) in triplicate (R1, R2, R3). Lane/Sample R1 was processed for GeLC-MS after visualization by Gel Doc EZ (left) or Coomassie staining and destaining (right).

Protein Electrophoresis and Collection of Individual Gel Slices. 50 µg protein from 3T3 whole cell lysates was electrophoresed on 4-15% Criterion Tris-HCl or Criterion TGX Stain-Free gels in triplicate. After electrophoresis, Tris-HCl gels were visualized by Coomassie staining and destaining (~3 hr). After destaining was completed, eight slices covering one single entire lane were cut and processed for in-gel trypsin digestion and post-digestion sample processing. In the case of samples run on TGX Stain-Free gels, gels were visualized using a Gel Doc EZ imager with 5 min UV activation and eight slices covering an entire single lane cut out identically as above for in-gel digestion and post-digestion peptide purification. Each gel slice was assumed to contain ~6 µg protein. See FIG. 2.

In-Gel Digestion (Adapted from Shevchenko et al. 1996). Gel slices were initially washed with water, twice with 1:1 100 mM $NH_4HCO_3$/acetonitrile for 15 min each, and then washed once with 2× volume of acetonitrile. Gel slices were rehydrated in 100 mM DTT/100 mM $NH_4HCO_3$, incubated at 56° C. for 1 hr and removed for cooling to room temperature. The liquid was removed and proteins alkylated by 50 mM iodoacetamide/100 mM $NH_4HCO_3$ for 30 min at room temperature in the dark. After removal of alkylating buffer, gel slices were washed with acetonitrile and $NH_4HCO_3$ as above, until all the Coomassie stain was removed. The last wash was performed with 100% acetonitrile and samples processed for in-gel trypsin digestion. Gel slices were rehydrated in 100 mM $NH_4HCO_3$, 5 mM $CaCl_2$, 1.5 ng/ml trypsin for ~20 min on ice. The supernatant was removed and replaced with 40-70 µl of the same buffer without trypsin and digestion continued overnight at 37° C.

Post-Digestion Peptide Purification (Adapted from Rappsilber et al. 2003). After overnight tryptic digestion in microcentrifuge tubes, samples were vacuum dried, reconstituted in ~0.2-0.4% TFA, and processed for C18 purification of peptides. Each gel slice was assumed to contain ~6 µg tryptic peptides and processed for C18 purification using 3 punches (made using an 18 gauge blunt tip syringe needle) of Empore reversed-phase extraction disks in a stage-tip. ~1.5 µg peptide was analyzed on a Velos Orbitrap mass spectrometer (Thermo Fisher Scientific) as described herein. Peptides were dissolved in 16.5 µL of load solvent (98:2: 0.01 water/acetonitrile/formic acid) and 5 µl loaded directly onto a 12 cm×75 µm fused silica pulled-tip capillary column packed in-house with Magic C18AQ, 5 µm, 200 Å pore size resin (Michrom BioResources, Inc.) with load solvent at a flow rate of 800 nl/min using a Nano LC-1D Plus system and a MicroAS autosampler. Peptides were eluted using a gradient of 10-40% acetonitrile in 0.1% formic acid over 55 min with a constant flow of 320 nl/min. The column was mounted in a nanospray source directly in line with a Velos Orbitrap mass spectrometer. Spray voltage was at 2.2 kV and the heated capillary maintained at 260° C. The orbital trap was set to acquire survey mass spectra (m/z 300-2000) with a resolution of 30,000 at m/z 400 with a target value set to 1E6 ions or 500 ms. The six most intense ions from the full scan were selected for fragmentation by higher-energy collision induced dissociation activation (normalized collision energy, 40% activation time 0.1 msec, fixed first m/z value at 111) in the HCD multipole with automatic gain control settings of 100,000 ion or 500 ms concurrent with full-scan acquisition in the orbital trap. For enhanced mass accuracy, the lock mass option was enabled for real-time calibration with polysiloxane peak at 445.1200 m/z. Precursor ion charge state screening was enabled; unassigned and singly charged species were rejected. Dynamic exclusion set to a maximum of 50 entries with a maximum retention period of 15 sec and mass window of −0.7 to 1.25 amu. Data were acquired using Xcalibur software v 2.1.0 SP1.

Figure 3:
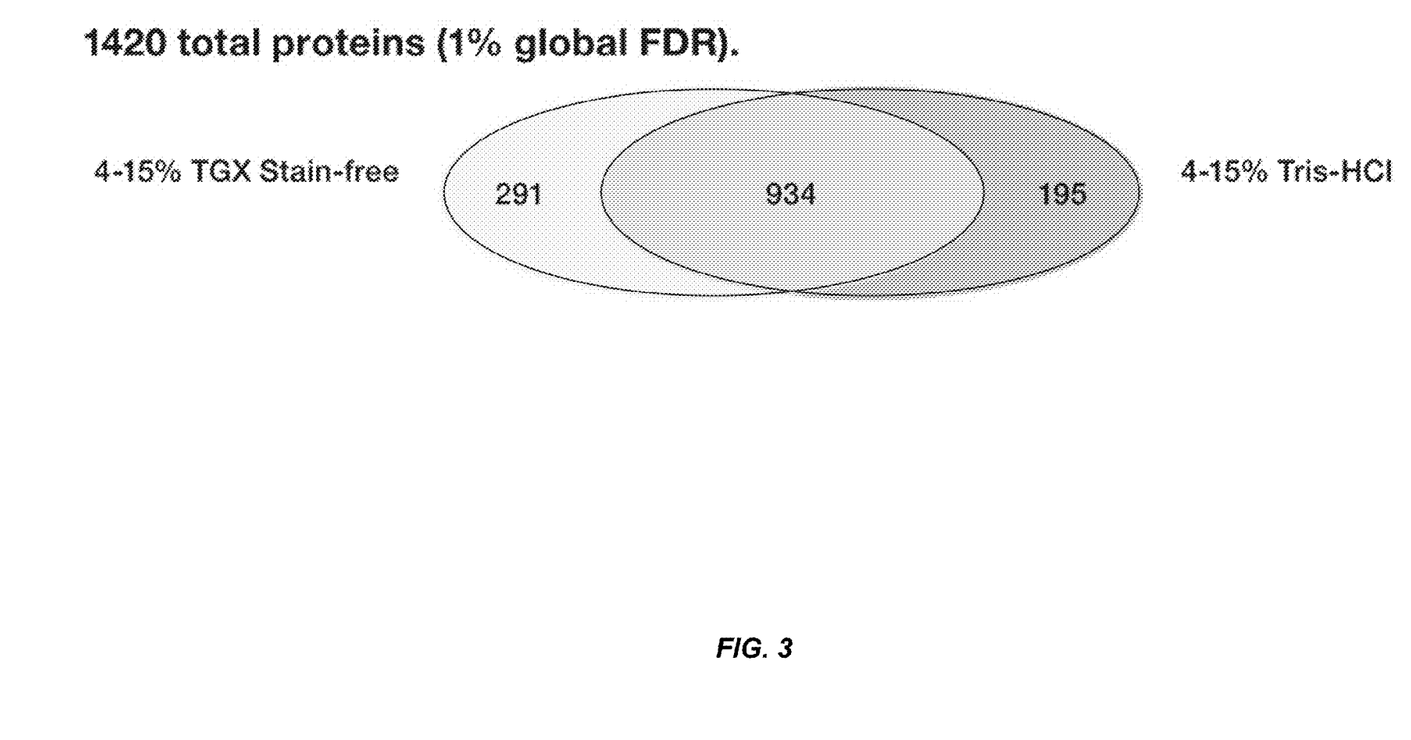
FIG. 3 shows overlap of GeLC-MS protein identifications between 4-15% Tris-HCl and 4-15% TGX Stain-Free gels. More additional proteins were identified using TGX Stain-Free gels than using Tris-HCl gels.

Database Searches. Collected spectra were searched against the 2011 version of the uniprot mouse database (47932) to which the reverse complement of each protein was appended along with common contaminants using SEQUEST V27Rev12. Fixed modifications used was +57 Da on Cys (alkylation by iodoacetamide) and variable modifications used were +16 Da Met (oxidation), +32 on Trp (formylkynurein), and +58 on Trp (hydroxylethanone). All protein identifications were filtered at 1% global false discovery rate (1% false discovery rate at protein level) using Scaffold Version 3.0. Results are presented in FIG. 3 and Table 1.

Coomassie is a trademark of BASF Aktiengellschaft. Empore is a trademark of 3M Company. Orbitrap is a trademark of Thermo Finnigan, LLC. MicroAs is a trademark of Thermo Fisher Scientific, NanoLC is a trademark of Eksigent Technologies.

TABLE 1

Results from GeLC-MS workflow using 4-15% Tris-HCl gels and 4-15% TGX Stain-Free gels.

| 4-15% Gel | Tris-HCl | TGX-Stain-Free |
|---|---|---|
| Stain-Free Proteins (1% global FDR) | 1,129 | 1,225 |
| Peptides (0.2% global FDR) | 15,541 | 15,802 |
| Spectra | 37,528 | 38,999 |
| % Identified spectra | 41 | 41 |

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method of preparing a protein sample for mass spectroscopy, wherein said protein sample is a complex protein sample comprising at least 50 different proteins, said method comprising:
   a) providing a one-dimensional (1D) electrophoresis gel comprising said complex protein sample, wherein proteins of said complex protein sample have been separated by electrophoresis in only one direction, and at least some proteins comprise tryptophan residues;
   b) contacting said complex protein sample of step a) with a halo-substituted compound;
   c) exposing said 1D electrophoresis gel to UV light, thereby reacting said tryptophan residues with said halo-substituted compound, covalently modifying said tryptophan residues, and rendering said tryptophan residues fluorescent;
   d) detecting fluorescence emitted from said 1D electrophoresis gel of step c);
   e) excising at least one portion of said 1D electrophoresis gel based upon detected fluorescence of step d), wherein said at least one portion comprises proteins of said complex protein sample and is excised from one lane of said 1D electrophoresis gel, wherein said excising comprises making cuts in said 1D electrophoresis gel around said at least one portion, thereby separating said at least one portion from the rest of said 1D electrophoresis gel; and
   f) subjecting proteins from said at least one portion of said 1D electrophoresis gel of step e) to mass spectroscopy, wherein more proteins are subjected to mass spectroscopy and detected by mass spectroscopy than would be if said 1D electrophoresis gel were contacted with a protein stain.

2. The method of claim 1, wherein said halo-substituted compound is a component of said 1D electrophoresis gel and said contacting of step b) occurs upon separating proteins of said complex protein sample by 1D electrophoresis.

3. The method of claims 1, wherein said halo-substituted compound is selected from the group consisting of chloroform, trichloroethanol, trichloroacetate, and 3-bromo-1-propanol.

4. The method of claim 1, wherein said UV light has a wavelength in the range of 200 nm to 400 nm.

5. The method of claim 1, wherein said exposing of step c) and said detecting of step d) occur simultaneously.

6. The method of claim 1, wherein the number of portions of said 1D electrophoresis gel excised is in the range of 1 to 30, 2 to 20, 5 to 15, or 6 to 12.

7. The method of claim 1, wherein multiple portions are excised from said 1D electrophoresis gel and said multiple portions are together coextensive with one lane of said 1D electrophoresis gel.

8. The method of claim 1, wherein said at least one portion of said 1D electrophoresis gel excised in step e) contains proteins with covalently modified tryptophan residues.

9. The method of claim 1, further comprising contacting said at least one portion of said 1D electrophoresis gel with a protease or alkylating agent after said excising said at least one portion of said 1D electrophoresis gel of step e).

10. The method of claim 9, wherein said protease is trypsin.

11. The method of claim 9, wherein said alkylating agent comprises iodoacetamide.

12. The method of claim 1, further comprising subjecting proteins, or fragments thereof, from said at least one portion of said 1D electrophoresis gel of step e) to further separation by liquid chromatography.

13. The method of claim 1, wherein said mass spectroscopy is LC-MS.

14. The method of claim 1, further comprising:
   detecting the masses of proteins or fragments thereof from said at least one portion of said 1D electrophoresis gel of step f) by mass spectroscopy; and determining the amino acid sequences of said proteins or fragments thereof, wherein said determining takes into account any changes in the masses of tryptophan residues due to covalent modifications from said halo-substituted compound.

15. The method of claim 1, further comprising extracting proteins from said at least one portion of said 1D electrophoresis gel of step e), wherein said extracting is performed after excising the at least one portion from said 1D electrophoresis gel and prior to subjecting proteins from said at least one portion of said 1D electrophoresis gel to mass spectroscopy.

16. The method of claim 1, wherein said at least one portion of said 1D electrophoresis gel of step e) contains all proteins of said complex protein sample.

17. The method of claim 1, wherein said excising of step e) comprises making cuts at the edges of one lane of said 1D electrophoresis gel, and in the direction of protein separation in said 1D electrophoresis gel.

18. The method of claim 1, wherein said 1D electrophoresis gel further comprises a molecular weight standard, and said at least one portion is excised from said 1D electrophoresis gel by making reference to said molecular weight standard.

19. The method of claim 1, comprising excising a plurality of portions of said 1D electrophoresis gel based upon detected fluorescence, wherein said plurality of portions are excised from the same lane of said 1D electrophoresis gel and correspond to different regions along the direction of protein separation in said 1D electrophoresis gel.

20. The method of claim 19, wherein said plurality of portions of said 1D electrophoresis gel are cut from the lane to have equal sizes.

* * * * *